US00PP17671P3

(12) United States Plant Patent
Gossett

(10) Patent No.: US PP17,671 P3
(45) Date of Patent: May 1, 2007

(54) *SEDUM* PLANT NAMED 'MR. GOODBUD'

(50) Latin Name: ***Sedum* hybrid**
Varietal Denomination: Mr. Goodbud

(75) Inventor: Gary J. Gossett, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 105 days.

(21) Appl. No.: 11/152,489

(22) Filed: Jun. 13, 2005

(65) Prior Publication Data

US 2006/0282924 P1 Dec. 14, 2006

(51) Int. Cl.
*A01H 5/00* (2006.01)

(52) U.S. Cl. ..... Plt./263
(58) Field of Classification Search ..... Plt./263
See application file for complete search history.

(56) References Cited

U.S. PATENT DOCUMENTS

PP16,350 P2 * 3/2006 Herdegen ..... Plt./263

OTHER PUBLICATIONS http://www.waysidegardens.com/webapp/wcs/stores/servlet/StoreCatalogDisplay?storeId=10151&catalogId=10151&langId=1&mainPage=prod2working&ItemId=46833.*

* cited by examiner

*Primary Examiner*—Wendy Haas
(74) *Attorney, Agent, or Firm*—Klarquist Sparkman, LLP

(57) ABSTRACT

A new and distinct hybrid of *Sedum* plant characterized by red tinted stems and foliage, a compact, upright habit, large red purple and mauve flowers, and prominent white flower buds.

1 Drawing Sheet

Botanical denomination: *Sedum* hybrid (*S. spectabile* 'Brilliant'×*S. telephium*).

Variety designation: 'Mr. Goodbud'.

The present invention relates to a new and distinct cultivar of *Sedum* hybrid and given the cultivar name of 'Mr. Goodbud'. *Sedum* is in the family Crassulaceae. *Sedum* 'Mr. Goodbud' originated from an open pollinated cross between *Sedum spectabile* 'Brilliant' as the seed parent (unpatented) and an unnamed plant of *Sedum telephium* as the pollen parent (unpatented).

This new and unique *Sedum* is distinguished by:

1. Large red purple and mauve flowers.
2. Prominent, almost white flower buds.
3. Red tinted stems and foliage.
4. Upright, compact growth habit.
5. Short stature.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows *Sedum* 'Mr. Goodbud' growing in the ground in August in the trial fields in Canby, Oreg.

DETAILED PLANT DESCRIPTION

The following is a detailed description of the new *Sedum* hybrid based on observations of one and a half year old specimen in September grown in the ground in full sun under typical outdoor conditions in the trial fields in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart.

Botanical classification: *Sedum* hybrid (*S. spectabile* 'Brilliant'×*S. telephium*).

Variety denomination: 'Mr. Goodbud'.

Plant:

*Type.*—Herbaceous perennial.
*Hardiness.*—USDA Zone 4 to 9.
*Size.*—34 cm tall from the ground to the top of the foliage and 45 cm wide.
*Habit.*—Compact, bushy.
*Vigor.*—Excellent.
*Root description.*—Multiple fleshy roots from each crown, Greyed Yellow 161C, grows to 5 mm wide and 20 cm long in clay loam soil.

Stem:

*Height.*—66 cm.
*Width.*—13 mm at base.
*Color.*—Varies from Yellow Green 146B in the shaded areas and Greyed Purple 183C in the sun.
*Texture.*—Succulent.
*Surface.*—Glaucous.

Leaf:

*Type.*—Simple.
*Arrangement.*—Opposite.

*Shape.*—Elliptic.
*Venation.*—Pinnate.
*Margins.*—Coarsely and irregularly serrate.
*Apex.*—Broadly acute.
*Base.*—Cuneate.
*Blade size.*—Grows to 13 cm long and 4.5 cm. wide.
*Surface.*—Glaucous.
*Texture.*—Thick, spongy, succulent.
*Petiole.*—Leaves sessile.
*Leaf color.*—Topside — Blue green (between Yellow Green147A and Greyed Green 147A) tinged on sun side with maroon (Greyed Purple 187B). The color is variable depending on light and stress conditions. Leaves are darkest in full sun and low water. Bottom side — Between Yellow Green147B and Greyed Green 147A.

Inflorescence:
*Type.*—Terminal, corymbose, umbel-like.
*Size.*—28 cm wide and 14 cm deep.
*Number of flowers.*—Up to 900 per main stem.
*Peduncle.*—Height — 20 cm. Diameter — 4 mm. Color — Varies from Yellow Green 146B in the shaded areas and Greyed Purple 183C in the sun. Texture — Succulent. Surface — Glaucous.
*Branching.*—Up to 6 main branches on one stem.
*Bloom period.*—Late August through September in Canby, Oreg.

Flower bud:
*Size.*—2.5 mm wide, 6 mm deep.
*Description.*—Ovoid.
*Color.*—White 155A.

Flower:
*Type.*—Complete, actinomorphic.
*Shape.*—Stellate.
*Size.*—9 mm deep and 15 mm wide.
*Petal count.*—5.
*Petal color.*—Mauve, between Greyed Purple 186C and Red Purple 72B.
*Petal shape.*—Lorate, reflexed.
*Petal size.*—8 mm long, 1.5 mm wide.
*Calyx.*—Divided 4/5ths of the way to the base, campanulate, 3 mm deep and 2.5 mm wide.
*Calyx color.*—Yellow Green 147B.
*Sepal number.*—5 lobes.
*Stamen number.*—5.
*Carpel.*—Prominent, 5 separate.
*Pistil size.*—6 mm deep and 1 mm wide.
*Pistil color.*—Greyed Purple 186A to C.
*Stamens.*—10, Greyed Purple 186B.
*Pollen color.*—No pollen, male sterile.
*Fragrance.*—None.
*Lastingness.*—Each corymb lasts about five weeks.

Fruit:
*Type.*—Ventrally dehiscent follicle, erect.
*Fertility.*—Sterile.
*Color.*—Brown 200A.

Seed: No seed made.

Pests and diseases: *Sedum* are susceptible to mealy bugs, scale insects, slugs and snails. No problems have been noted for this variety. All *Sedum* will develop root rot in wet conditions.

COMPARISON TO SIMILAR *SEDUM*

Compared to the seed parent, *Sedum spectabile* 'Brilliant', *Sedum* 'Mr. Goodbud' has darker foliage and stem and smaller inflorescences with duller pink flowers. They have similar habits. *Sedum* 'Mr. Goodbud' has strong stems that do not flop over after it blooms.

Compared to *Sedum* 'Ruby Glow', an unpatented plant, *Sedum* 'Mr. Goodbud' has a more upright habit and has noticeable, white, flower buds.

I claim:

1. A new and distinct hybrid of *Sedum* plant as herein illustrated and described.

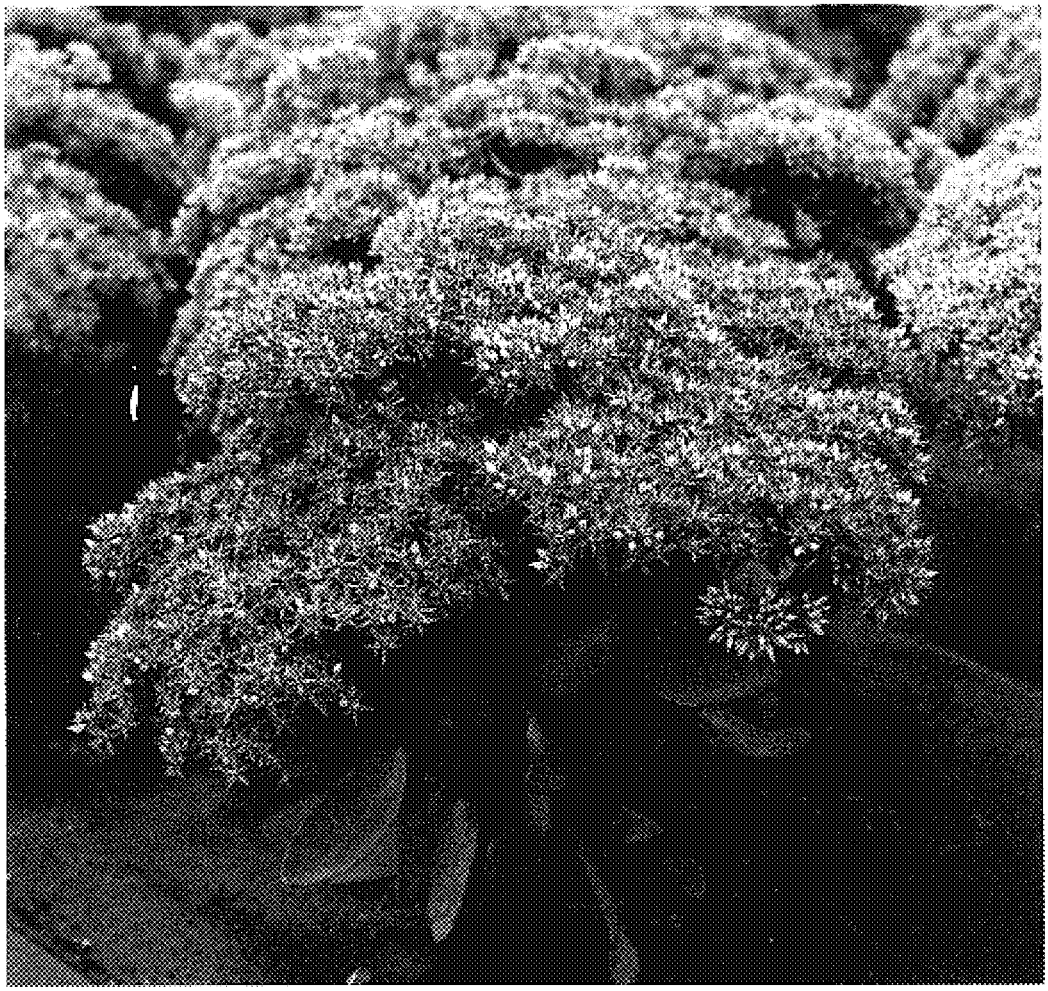

* * * * *